US008814569B2

(12) United States Patent
Carvalho

(10) Patent No.: US 8,814,569 B2
(45) Date of Patent: Aug. 26, 2014

(54) FIXTURE FOR ANCHORING IN JAW BONE

(75) Inventor: Paulo Malo Carvalho, Lisbon (PT)

(73) Assignee: Nobel Biocare Services AG, Zurich-Flughafen (CH)

( * ) Notice: Subject to any disclaimer, the term of this patent is extended or adjusted under 35 U.S.C. 154(b) by 0 days.

(21) Appl. No.: 11/250,900

(22) Filed: Oct. 14, 2005

(65) Prior Publication Data

US 2006/0115791 A1 Jun. 1, 2006

Related U.S. Application Data

(63) Continuation of application No. PCT/SE2004/000532, filed on Apr. 6, 2004.

(30) Foreign Application Priority Data

Apr. 17, 2003 (SE) ........................................ 0301149

(51) Int. Cl.
*A61C 8/00* (2006.01)

(52) U.S. Cl.
USPC .......................................... 433/174; 433/173

(58) Field of Classification Search
USPC .......... 433/172–176; 411/393, 411, 424, 426, 411/DIG. 1
See application file for complete search history.

(56) References Cited

U.S. PATENT DOCUMENTS

| | | | | |
|---|---|---|---|---|
| 5,032,129 | A * | 7/1991 | Kurze et al. ................. | 623/23.49 |
| 5,642,996 | A * | 7/1997 | Mochida et al. ............... | 433/174 |
| 5,702,346 | A * | 12/1997 | Lazzara et al. ................ | 433/173 |
| 6,375,465 | B1 | 4/2002 | Engman et al. | |
| 6,406,296 | B1 * | 6/2002 | Hollander et al. ............. | 433/174 |
| 6,846,180 | B1 * | 1/2005 | Joos ............................... | 433/174 |
| 6,918,766 | B1 * | 7/2005 | Hall et al. ................... | 433/201.1 |
| 7,008,227 | B2 * | 3/2006 | Carmichael et al. .......... | 433/174 |

FOREIGN PATENT DOCUMENTS

| | | |
|---|---|---|
| EP | 1 030 622 | 2/2006 |
| EP | 1 617 782 | 1/2012 |
| WO | WO 9743976 A1 | 11/1997 |
| WO | WO 99/23971 | 5/1999 |

(Continued)

OTHER PUBLICATIONS

International Search Report for Application No. PCT.SE2004/000532 (the PCT counterpart of the parent application).

*Primary Examiner* — Todd Manahan
*Assistant Examiner* — Michael R Ballinger
(74) *Attorney, Agent, or Firm* — Knobbe, Martens, Olson & Bear, LLP

(57) ABSTRACT

To anchor a fixture in a jaw bone, the fixture is applied in a hole which is substantially smaller than the diameter of the fixture. The fixture has a front portion which from the point of view of diameter grows very much narrower and which is arranged with both a cutting function and a threading function. The fixture is provided with a thread, with one, two or more thread turns extending down along the greatly narrowing portion while substantially maintaining their thread profile. One or more porous layers arranged on the thread turns can also be included. In this way the fixture can exploit the clamping effect from the soft parts of the jaw bone and still effectively penetrate through any hard parts possibly present in the jaw bone, without these hard parts being pressed inward upon fixture application. An effective fusion of the fixture in the jaw bone is achieved with the aid of said porous outer layers.

14 Claims, 3 Drawing Sheets

(56) References Cited

FOREIGN PATENT DOCUMENTS

| WO | WO 0053117 A1 | | 9/2000 |
| WO | WO 01/49200 | | 7/2001 |
| WO | WO 0149200 A2 | | 7/2001 |
| WO | WO 01/74412 | * | 10/2001 |
| WO | WO 03/003937 | | 1/2003 |
| WO | WO 2004/012622 | | 2/2004 |

* cited by examiner

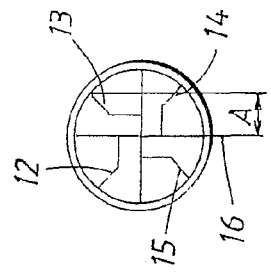
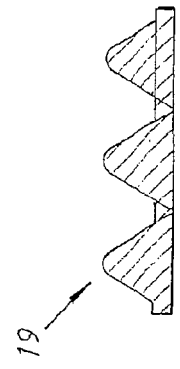
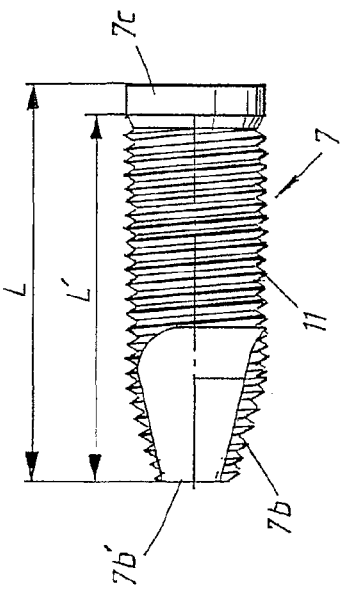
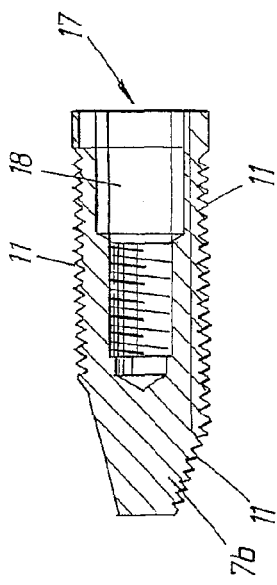
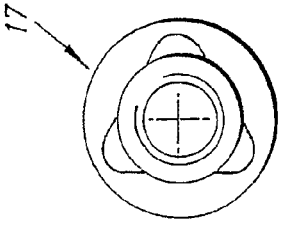
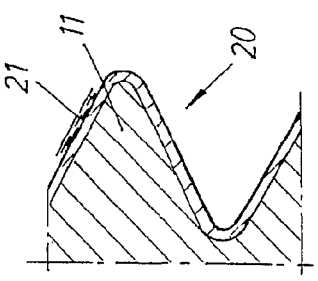

FIXTURE FOR ANCHORING IN JAW BONE

PRIORITY INFORMATION

This application is a continuation of International Application PCT/SE2004/000532, with an international filing date of Apr. 6, 2004, which claims priority under 35 U.S.C. §119 to Swedish Patent Application No. 0301149-1, filed Apr. 17, 2003, the entire contents of which are expressly incorporated by reference herein.

BACKGROUND OF THE INVENTION

1. Field of the Invention

The present invention relates to an arrangement in the form of a fixture for effective anchoring even in a jaw bone with a combination of soft and hard bone portions (or inlays/grafts), which fixture can be applied in a hole having a diameter smaller than the diameter of the fixture in order to produce a clamping effect on the implant from the soft bone portion or portions.

2. Description of the Related Art

It is already known to adapt implants individually to soft and hard bones. Various implants and methods have been proposed to meet the different requirements which arise in hard jaw bone and soft jaw bone situations, and two different implant types and implant characters have in principle been used for the two different bone types.

For example, in a fixture or implant exclusively for soft jaw bone, it is possible to use a slightly conical implant in accordance with Swedish patent 516 917 obtained by the same Applicant as is filing the present application. The implant is in this case provided with thread turns which permit excellent integration with the bone substance and prevent breaking-off of fine bone trabeculae when the fixture is being screwed into the bone.

However, there are clinical situations in which soft jaw bone may be present in combination with hard jaw bone portions or grafts with different degrees of hardness, which are located like islands amid the softer jaw bone. The present-day fixtures for soft bone which are applied in holes with a smaller diameter than the fixtures concerned have a limited ability to expand and penetrate the hard bone portions or equivalent in question, and instead have the result that the fixtures press the hard bone portions aside. In addition, the hard bone portions may interfere with the threading of the bone. All of this can result in unsatisfactory or defective fixture installations.

SUMMARY OF THE INVENTION

An object of the present invention is to solve the problem described above, inter alia, and in one embodiment it proposes a fixture arrangement which is suited both for exclusively soft jaw bone portions and also for soft jaw bone portions where there are also hard jaw bone parts or equivalent. An embodiment of the invention also goes further and proposes that the novel fixture structure for promoting the firm attachment of the fixture in the jaw bone.

In one embodiment, a dental implant comprises a front portion which from the point of view of diameter grows very much narrower and which is arranged with both a cutting function and a threading function and is thus able, upon contact with a hard bone portion or portions, to penetrate through these without causing any substantial tendency for displacement of the respective hard bone portion. Another embodiment, a further feature is that the thread, which can have one, two or more thread turns, extends along the greater part of the outer surface of the fixture and also down along the greatly narrowing portion while substantially maintaining its thread profile.

In yet another embodiment, a further feature is that the fixture is specifically adapted for holes with a considerably smaller diameter than the main diameter of the fixture. This is achieved by the greatly narrowing design of the tip, which facilitates entry even into under-prepared areas.

Another embodiment of the present invention comprises a dental implant for effective anchoring in a jaw bone with a combination of soft and hard bone portions or inlays. The implant is configured to be applied in a hole with a diameter that is substantially smaller than the diameter of the implant so as to produce a clamping effect on the implant from the soft bone portions. The implant comprises a proximal portion and a tapering front portion. The tapering front portion has an end surface, which from the point of view of the diameter of the implant is substantially narrower. The front portion comprises a cutting edge that is configured, upon contact with the hard bone portions, to penetrate through the hard bone portions without causing a substantial tendency for displacement of the implant, and a threaded portion which has at least one thread turns and extends from the proximal portion of the implant to the front portion while substantially maintaining a thread profile.

An advantage of the embodiments describe above is that they permit, in comparison with existing products, improved application of an implant into both in soft bone and also in soft bone with interspersed portions of hard bone.

According to a preferred embodiment, one or more porous outer layers are used which are arranged on the thread/thread turns and which ensure effective fusion of the fixture in the jaw bone.

With the above-described embodiments is thus possible to satisfy the abovementioned requirements for a much effective fixture installation. Double or multiple threads can be obtained by proven techniques and a more prominent feature in this respect is that the double or multiple thread will extend downward along the greatly narrowing front portion whose cutting function can also be designed in a known manner. The front end can effectively enter and penetrate through hard areas of the jaw bone when the fixture is being screwed into the hole. The proposed porous layers can be formed in a known manner. For example, they can consist of oxide layers of the type included in the TiUnit® fixtures sold on the market by Nobel Biocare.

Certain objects and advantages of the invention have been described above for the purpose of describing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

BRIEF DESCRIPTION OF THE DRAWINGS

A general architecture that implements various features of specific embodiments of the invention will now be described with reference to the drawing. The drawing and the associated descriptions are provided to illustrate embodiments of the invention and not to limit the scope of the invention.

FIG. 2 is a side view showing an embodiment of the fixture.

FIG. 3 is a longitudinal section showing the fixture according to FIG. 2.

FIG. 4 is an end view of FIG. 2, showing the cutting edges arranged on the fixture.

FIG. 5 is another end view of the fixture according to FIG. 2, showing the arrangement for application of screwing tools.

FIG. 6 is a longitudinal section showing parts of a thread with double turns arranged on the fixture.

FIG. 7 is a vertical section showing parts of the thread structure on the fixture according to FIG. 2.

DETAILED DESCRIPTION OF THE PREFERRED EMBODIMENTS

Figure 1:
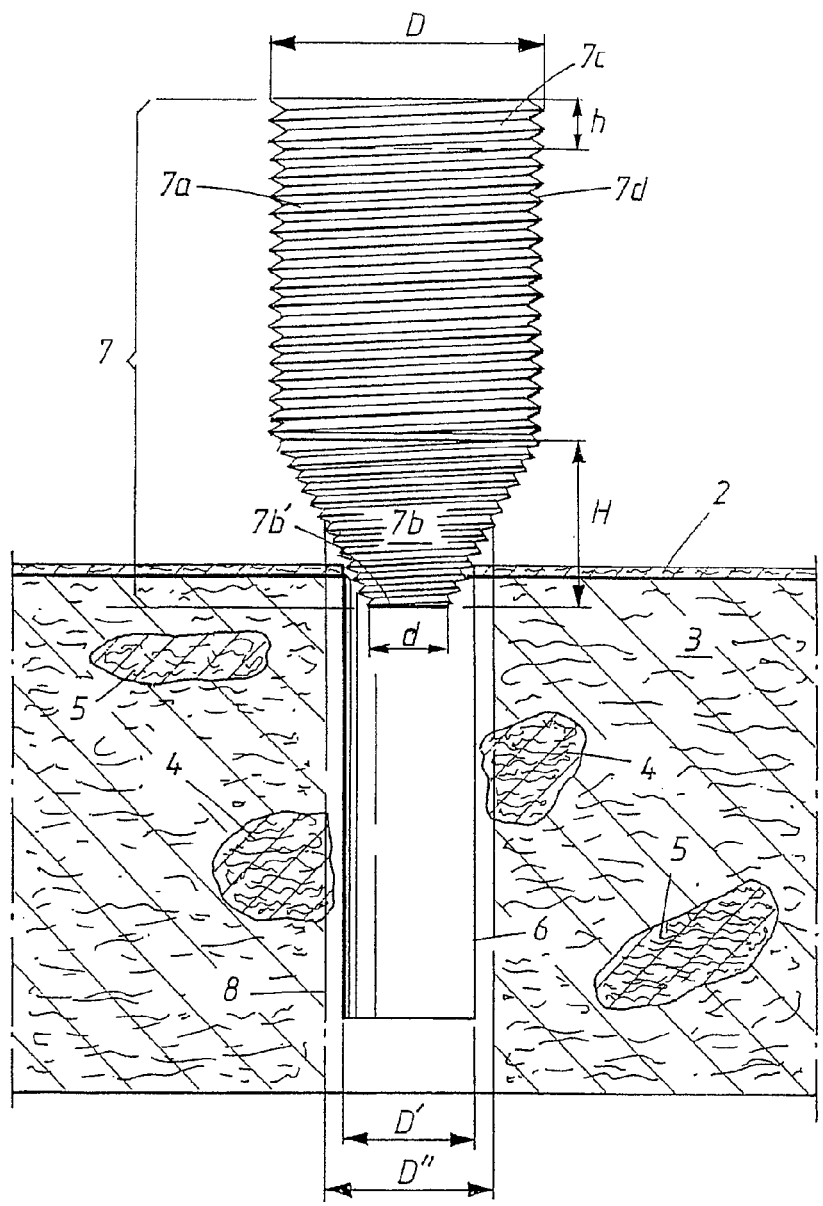
FIG. 1 is a vertical cross section showing the fixture in association with a jaw bone having different degrees of hardness.

In FIG. 1, a jaw bone is indicated diagrammatically by reference number 1. The jaw bone can comprise different portions of bone. For example, a first layer of hard bone having been indicated by reference number 2, a second predominant layer of soft bone indicated by reference number 3, and islands of harder bone indicated by reference numbers 4 and 5. A hole 6 has been arranged in a manner known per se in the jaw bone. An illustrated embodiment of a fixture or dental implant 7, which is to be screwed into the hole, is also shown. The fixture 7 has a first or proximal part 7a which can be cylindrical or slightly conical. The fixture 7 also comprises a front or distal portion 7b which narrows greatly toward its front or distal end, from the point of view of its diameter. The fixture 7 also includes a collar-like attachment part 7c of substantially the same diameter D as the cylindrical part 7a.

The front end surface 7b' on the front, greatly narrowing portion 7b has an end surface diameter d. In one embodiment, D has a value of about 4 mm, and d has a value of about 2 mm. The portion 7b has a height H which substantially corresponds to the diameter value d. The collar-shaped part 7c has a height h of about 1-3 mm. The configuration shown means that the fixture 7 can enter holes 6, 8 with different diameters D' and D" which are much smaller than the main diameter D of the fixture and can penetrate through the actual portion or portions of hard bone, for example the bone portion or the islands 4, 5. The arrangement means that the fixture can expand and also penetrate through hard bone portions and still cooperate with soft bone portions, for example the bone area 3, so that this applies clamping forces against the side surface 7d of the fixture.

In accordance with FIG. 2, the fixture 7 is provided with an outer thread 11, preferably with two or more thread turns. Apart from the collar part 7c, the thread 11 extends along the remaining length L' of the fixture, i.e. also down along the portion 7b to its end 7b". The total length of the implant 7 is indicated by L. According to FIG. 4, the illustrated fixture 7 is provided with four cutting edges 12, 13, 14 and 15. A distance between the outer margin of the edge 13 and the center line 16 of the fixture is indicated by A.

Figure 1A:
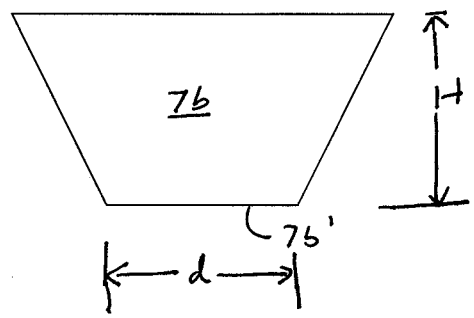
FIG. 1A is a schematic side view of a distal end of modified embodiment of the implant of FIG. 1.

FIG. 1A is a schematic side view of a distal end of modified embodiment of the implant of FIG. 1. In this embodiment, the front portion 7b has a height (H) which is substantially equal to the diameter (d) of the end surface 7b'.

Figure 1B:
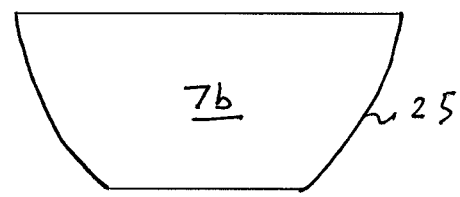
FIG. 1B is a schematic side view of a distal end of another modified embodiment of the implant of FIG. 1.

FIG 1B is a schematic side view of a distal end of another modification embodiment of the implant of FIG. 1. In this embodiment, the front portion 7b has a curved lateral surface 25.

FIG. 5 shows an arrangement for applying a turning or screwing tool (not shown). The arrangement has been symbolized by 17 and can be formed in a manner known per se, for which reason it will not be described in detail here.

FIG. 3 shows the fixture 7 in longitudinal section, depicting the lines of the front portion 7b and of the double threads 11. The fixture has inner recesses 18 for said tightening arrangement 17 and for application of superstructures which are to be applied to the fixture after it has been installed in the jaw bone.

FIG. 6 shows an example of the thread profile 19, for instance a thread with two thread turns. As the technique according to Swedish patent 516 917, which is incorporated by reference in its entirety herein, can be used for producing the double thread in question, the arrangement will not be described in detail here, and instead reference is made to the patent in question.

FIG. 7 shows the case where the thread arrangement 11 in accordance with an embodiment of the invention is provided with a porous layer symbolized by 20. The production of porous layers of this kind has also been described in detail by the same Applicant as is filing the present invention, and for this reason reference is made to these patents (see e.g., WO 2005/055858, which is hereby incorporated by reference herein in its entirety). In one embodiment, the porous layer can constitute a magazine for a bone-growth-stimulating substance or agent 21. This too is known per se and is set out in the last-mentioned patent.

In one illustrative embodiment, the total length L of the implant can be about 9.25 mm, and the threaded length L' can be of the order of about 7.75 mm.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A dental implant for supporting a dental prosthesis, said implant comprising:
   a proximal portion with a proximal end, the proximal portion being generally cylindrical and having a diameter of 4 mm; and
   a tapering front portion defining a proximal diameter and having a distal end surface that defines a distal diameter, the distal diameter being smaller than the proximal diameter, the front portion tapering linearly from the proximal diameter to the distal diameter, the distal diameter being 2 mm and being equal to a height of the tapering front portion, the front portion further comprising at least one cutting edge that extends from the distal end surface proximally into the proximal portion of the implant; and at least one thread that extends from the proximal portion of the implant to the front portion, the thread defining a thread height and a cross-sectional thread form that are constant along the extent of the thread on at least the tapering front portion of the implant.

2. The implant as claim 1, wherein the front portion comprises a plurality of cutting edges.

3. The implant of claim 1, wherein the thread height and the cross-sectional thread form are substantially constant along the extent of the thread on the proximal portion.

4. The implant of claim 3, wherein the thread height and the cross-sectional thread form along the extent of the thread on the proximal portion are the same as the thread height and the cross-sectional thread form along the extent of the thread on the tapering front portion.

5. The implant of claim 1, wherein the thread defines a thread angle that is constant along the extent of the thread on at least the tapering front portion of the implant.

6. The implant of claim 5, wherein the thread angle is constant along the extent of the thread on the proximal portion of the implant.

7. A dental implant for supporting a dental prosthesis, said implant comprising:
a proximal portion with a proximal end, the proximal portion having a diameter of 4 mm;
a tapering front portion defining a first diameter at a proximal end thereof and having a distal end surface with a second diameter that is 2 mm a height of the tapering front portion is 2 mm, the front portion further comprising a cutting edge that extends from the distal end surface to the proximal portion; and at least one thread that extends from the proximal portion of the implant to the front portion thereof, the thread defining a thread height and a cross-sectional thread form that are constant along the extent of the thread on at least the tapering front portion of the implant.

8. The implant as in claim 7, wherein the front portion tapers linearly from the first diameter to the second diameter.

9. The implant as in claim 7, wherein the front portion comprises a plurality of cutting edges.

10. The implant as in claim 7, wherein the proximal portion is cylindrical.

11. The implant of claim 7, wherein the thread height and the cross-sectional thread form are constant along the extent of the thread on the proximal portion.

12. The implant of claim 11, wherein the thread height and the cross-sectional thread form along the extent of the thread on the proximal portion are the same as the thread height and the cross-sectional thread form along the extent of the thread on the tapering front portion.

13. The implant of claim 7, wherein the thread defines a thread angle that is constant along the extent of the thread on at least the tapering front portion of the implant.

14. The implant of claim 13, wherein the thread angle is constant along the extent of the thread on the proximal portion of the implant.

* * * * *

UNITED STATES PATENT AND TRADEMARK OFFICE
CERTIFICATE OF CORRECTION

| | | |
|---|---|---|
| PATENT NO. | : 8,814,569 B2 | Page 1 of 1 |
| APPLICATION NO. | : 11/250900 | |
| DATED | : August 26, 2014 | |
| INVENTOR(S) | : Paulo Malo Carvalho | |

It is certified that error appears in the above-identified patent and that said Letters Patent is hereby corrected as shown below:

In the Specification

In column 2 at line 52, Change "uriderstood" to --understood--.

In column 3 at line 59, Change "7b"." to --7b'.--.

In column 4 at line 2, Change "modification" to --modified--.

In the Claims

In column 5 at line 10, In Claim 2, change "as" to --of--.

In column 5 at line 13, In Claim 3, after "are" delete "substantially".

Signed and Sealed this
Fourteenth Day of April, 2015

Michelle K. Lee
*Director of the United States Patent and Trademark Office*